(12) United States Patent
Turpin

(10) Patent No.: US 9,672,486 B1
(45) Date of Patent: Jun. 6, 2017

(54) INSPECTION TOOL

(71) Applicant: Pro-Kleen, Inc., Augusta, KS (US)

(72) Inventor: Kevin Turpin, Augusta, KS (US)

(73) Assignee: PK Companies Group, LLC, Wichita, KS (US)

( * ) Notice: Subject to any disclaimer, the term of this patent is extended or adjusted under 35 U.S.C. 154(b) by 697 days.

(21) Appl. No.: 13/668,040

(22) Filed: Nov. 2, 2012

Related U.S. Application Data

(60) Provisional application No. 61/554,906, filed on Nov. 2, 2011.

(51) Int. Cl.
| | | |
|---|---|---|
| *G06Q 10/06* | (2012.01) | |
| *H04N 7/18* | (2006.01) | |
| *G01N 21/88* | (2006.01) | |
| *G06T 7/00* | (2006.01) | |

(52) U.S. Cl.
CPC ....... *G06Q 10/06316* (2013.01); *G01N 21/88* (2013.01); *G01N 21/8851* (2013.01); *G06Q 10/06311* (2013.01); *H04N 7/185* (2013.01); *G01N 2021/888* (2013.01); *G01N 2021/8861* (2013.01); *G01N 2021/8864* (2013.01); *G01N 2021/8887* (2013.01); *G01N 2203/006* (2013.01); *G01N 2203/0069* (2013.01); *G06T 7/0002* (2013.01); *G06T 7/0004* (2013.01)

(58) Field of Classification Search
CPC ............... G01N 21/88; G01N 21/8803; G01N 21/8851; G01N 21/892; G01N 2021/8854; G01N 2021/8858; G01N 2021/8861; G01N 2021/8864; G01N 2021/888; G01N 2021/8887; G01N 2021/8893; G01N 2021/889; G06Q 10/06316; G06Q 10/06311; H04N 7/185
USPC ........................................................ 348/125
See application file for complete search history.

(56) References Cited

U.S. PATENT DOCUMENTS

| | | | | |
|---|---|---|---|---|
| 6,421,571 | B1 * | 7/2002 | Spriggs ................. | G05B 15/02 |
| | | | | 345/629 |
| 7,565,306 | B2 * | 7/2009 | Apostolides ................ | 705/7.26 |
| 8,315,834 | B2 * | 11/2012 | Gimelfarb .......... | G01B 11/0683 |
| | | | | 702/171 |
| 8,358,903 | B1 * | 1/2013 | Meads et al. ................. | 386/200 |
| 2004/0034684 | A1 * | 2/2004 | Payne ............................ | 709/201 |
| 2004/0262387 | A1 * | 12/2004 | Hart ....................... | G06Q 10/06 |
| | | | | 235/384 |
| 2005/0023347 | A1 * | 2/2005 | Wetzel et al. ................. | 235/385 |
| 2005/0137829 | A1 * | 6/2005 | Gimelfarb .......... | G01B 11/0683 |
| | | | | 702/171 |
| 2005/0211777 | A1 * | 9/2005 | Wetzel et al. ................. | 235/385 |
| 2006/0162178 | A1 * | 7/2006 | Freidin ............................ | 33/784 |
| 2006/0259392 | A1 * | 11/2006 | Rabenold ............... | G06Q 10/10 |
| | | | | 705/37 |

(Continued)

*Primary Examiner* — Gelek W Topgyal
(74) *Attorney, Agent, or Firm* — Erise IP, P.A.

(57) ABSTRACT

Disclosed is a web-based tool for facilitating the inspection process for evaluating inspection items relating to assets at a site. A website is used to interface with the hand held devices used by inspectors in the field and create consistency in the way questions are posed, and recorded for inspection items. Unique identifiers are associated with each item so that they can be tracked. Also, a wireless camera arrangement is implemented where any photographs taken of a condition of a particular inspection item will automatically be incorporated into the form open regarding that item.

17 Claims, 11 Drawing Sheets

(56) References Cited

U.S. PATENT DOCUMENTS

| | | | |
|---|---|---|---|
| 2007/0044559 A1* | 3/2007 | Andrews | 73/584 |
| 2008/0048682 A1* | 2/2008 | Brusco | G01B 21/08 324/700 |
| 2008/0077512 A1* | 3/2008 | Grewal | G05B 19/05 705/28 |
| 2008/0084291 A1* | 4/2008 | Campion et al. | 340/514 |
| 2008/0111074 A1 | 5/2008 | Weir et al. | |
| 2009/0018859 A1 | 1/2009 | Purifoy et al. | |
| 2010/0088141 A1* | 4/2010 | Hill | 705/8 |
| 2010/0306085 A1* | 12/2010 | Schmidt et al. | 705/28 |
| 2011/0016319 A1* | 1/2011 | Lundberg | G06F 21/83 713/170 |
| 2012/0109660 A1 | 5/2012 | Xu et al. | |

* cited by examiner

INSPECTION TOOL

CROSS-REFERENCE TO RELATED APPLICATIONS

This application claims the benefit of U.S. Provisional Patent Application No. 61/554,906 filed Nov. 2, 2011, the disclosure of which is incorporated herein by reference.

BACKGROUND

1. Field of the Invention

The present invention relates to the field of conducting inspections. More specifically, the present invention relates to the implementation of a facilitating web-based computer system and processes for creating uniformity in the way inspection forms are utilized, and in automatically incorporating photos and other information along with the forms presented.

2. Description of the Related Art

Some facilities require periodic inspections. In some instances these inspections are intended to detect an asset condition, e.g., degradation. A typical site may include thousands of various components which need to be independently evaluated to make sure they still have the desired properties. For example, where the property is existence of ample fire protection coatings, a particular asset, e.g., beam, vessel, or other metal component will be viewed and detailed notes taken regarding properties relating to the existence of coating, and other indications of degradation.

It is known for some inspectors to use portable computing devices to assist with the inspection process. In doing so, these inspectors may take either paper or electronic Adobe copies of the site schematics (e.g., plant) so that they can find locations of the assets to be inspected. Once located, the inspectors visually inspect the various components/assets and document the condition of different assets, e.g., metal supports, vessels, etc. This is sometimes done by recording the visual inspection results into a report, which can be saved after completion into the computing device. The inspector may also take photographs to document the condition of the assets.

Once the onsite work is completed, the inspector typically returns to the office, and completes a comprehensive report using the information obtained on the platform or other site. Also, the inspector will somehow associate the photos taken with whatever information is related to the same assets which were photographed. E.g., into a common file in My Documents on the PC, or into a physical paper file. This takes considerable time, but in the end, the report is completed, and kept for future reference.

If, in the future, reference need be made of the report, the interested party uses the hard copy site schematics for the purpose of locating the assets, and then must engage in a matching up of the asset components evaluated in the old report against those shown in the hard copy site schematic. This makes the process of comparing changes in degradation from one inspection to the next a time consuming and sometimes error prone ordeal.

SUMMARY

Disclosed is a tool for conducting inspections. In embodiments, the tool includes an inspection-item presenting process operating on a hand held computing device, e.g, an iPad, smartphone, laptop computer, or other computing device. The inspection-item presentation process causes the display of a map showing a plurality of assets from a facility. The selection of an asset from the map (which can be a plan view, sky view, or 3-D rendering) brings up a list of selectable inspection items related to the asset. Each inspection item, in some embodiments, is associated with a unique identifier.

The selection of a particular inspection item also brings up an information-gathering process. This process opens up an inspection form for the particular item selected. The form poses standardized questions relating to a condition of the asset.

If photos are helpful to the particular inspection item, the inspector can initiate a camera-interfacing process by hitting a button. In embodiments, the signal will cause any photos taken to be automatically downloaded into the handheld device, and then incorporated into the open inspection form. In a first embodiment a wireless camera is used. In others, the camera used is an on-board camera physically on the hand held device. Once the inspection form is completed by the inspector, the saving (locally) of this form results in the ceasing of downloads from the camera being used.

The standardized questions for the inspection items are set up in advance. The same questions can be used for the same type of inspection item, maintaining consistency. Further, the same questions can be repeatedly used in subsequent inspections, maintaining consistency over time.

A unique identifier is used for each inspection item such that a form for that item, the standardized questions posed, any photos taken, and any answers to the questions will be associated and archived with the unique identifier.

A prepopulation process is provided where some already-known parameters regarding the inspection (e.g., measurements and other parameters) are included into the form before the form is presented to the inspector. In embodiments, these prepopulated aspects are changeable on site by the inspector if they turn out to be incorrect or outdated.

In addition to or instead of the camera, a thickness reading device can be used. A process is provided that, when activated by hitting an on/off button displayed allowed the hand held to communicate (via Bluetooth) and download thickness readings from the thickness reading device. The thickness-reading-device-interfacing processes automatically incorporate thickness readings taken using the reader into the inspection form.

To ensure that the inspection questions have been answered for each inspection item, an inspection-completion-assurance process requires an inspector to answer all of the standardized questions posed for the particular inspection item before the form can be saved locally.

Embodiments also include a web-based process running on a network device operated by an inspection facilitator. The web-based process allows for the uploading by an inspector from the hand-held computing device of a plurality of completed inspection-item forms (e.g., all or part of a work order) onto a database maintained by the inspection facilitator.

Embodiments also include a cost-projection process wherein a plurality of answers to the standardized questions posed are accepted as inputs into cost formulas to calculate projected costs.

Embodiments also include a web based risk-prioritization process wherein a plurality of answers to the standardized questions posed are used to navigate a decision tree to reach a ranking in order of need for repair of the inspection items. In some instances the rankings are color coded. The risk-prioritization process also includes a cost cutoff process wherein a predetermined budget is applied to a higher-ranked group of inspection items and denied to a lower-ranked group of inspection items.

Another aspect disclosed in this application relates to a system. More specifically, a web-based inspection system maintained by an inspection facilitator. The system uses a web-connected computing system running a transmitting process which sends an inspection work (over the internet) to a hand held computing device operated by a inspector. The work order transmitted includes a facility map as well as a list of inspection items at that facility. The map shows facility assets which, when selected, will bring up the list of inspection items relevant to that asset. Selecting one of the listed items brings up standardized questions on a form relating to the selected inspection item.

A data-receiving process is also a part of the web-based system. The data-receiving process receives answers to the standardized questions for at least some of the inspection items and prioritizes them by need for repair according to a decision tree.

The web-connected computing system also includes an archiving database. All of the inspection data is archived by the unique identifier for each inspection item. This method of archiving ensures that the standardized questions posed will be repeated consistently, and that the answers given can be used as a good foundation for future trend analysis. More specifically, given the repeated consistently from inspection to inspection over time, the answers retrieved, when compared against different inspections, will reveal periodic changes in characteristics (e.g., wear, degradation) that can be useful for predicting and other analytical purposes.

DETAILED DESCRIPTION

Figure 1:
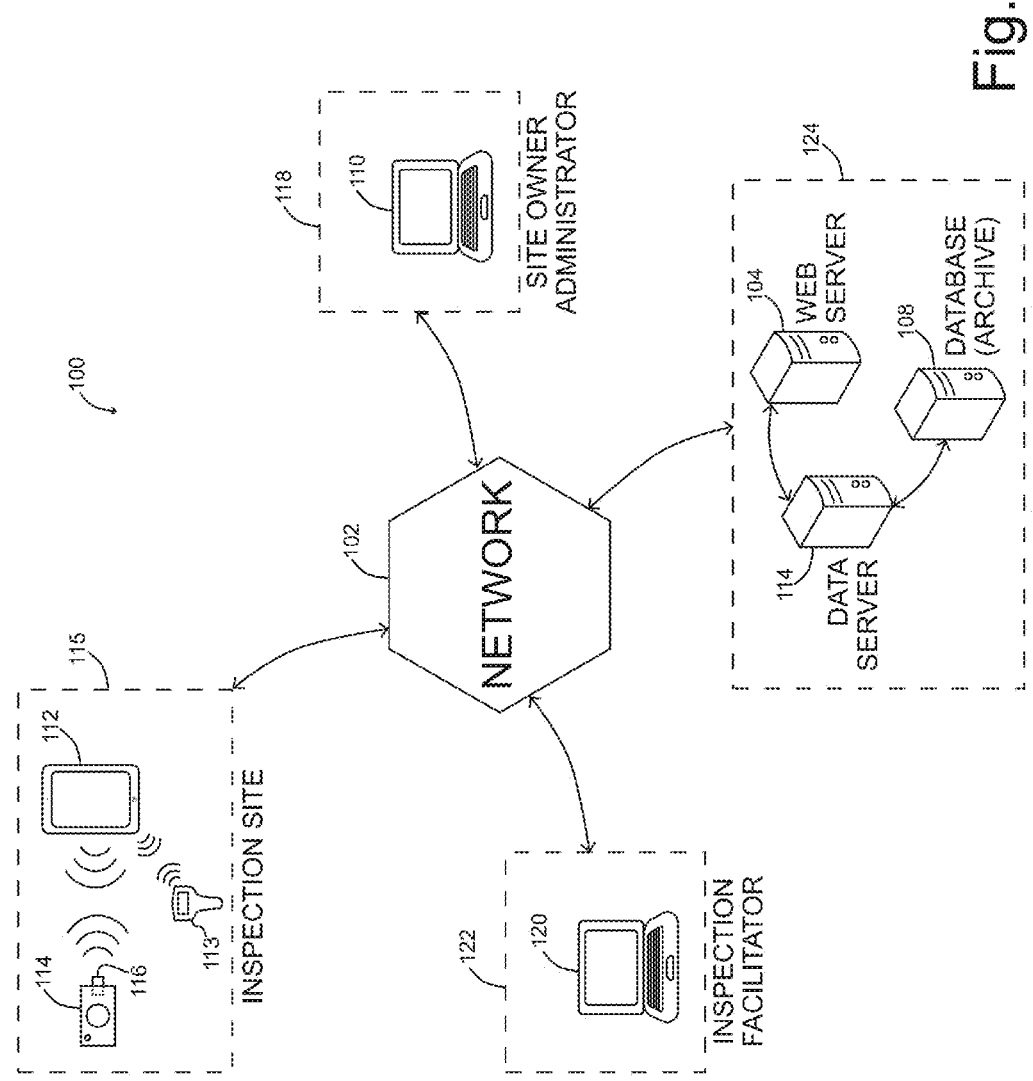
FIG. 1 illustrates a system diagram for a computing environment in which one embodiment of the disclosed processes could be performed.

Disclosed is a process for inspecting assets. More specifically, the process relates to the inspection of one or more assets at a facility. The inspector, wherever he or she has internet connectivity, downloads a number of things from the website related to an inspection list/work order. The download includes maps, questions, asset information (i.e., data sheets), sizes, material types, and other information relevant to the work order.

Then, with the work order information downloaded onto the portable computing device, e.g., a handheld computer, iPad, etc., the inspector goes out the site. The inspector can locate assets using selectable maps. Once at a physical location for an inspection of an asset, the inspector clicks on the asset in the map. This brings up an inspection list relevant to that asset, and a detailed map that provides asset locations which, when clicked on, will bring up a relevant list of inspection items. Clicking on a particular listed inspection item then will bring up an inspection form relating to that particular item.

With the form now displayed on the portable computing device, the inspector answers questions regarding that inspection being made of the asset. Also, if photos are needed, the inspector turns on camera-recognizing Wi-Fi features using an on/off button (color changing camera icon) included in the computer generated form. This causes the hand held computer 112 (see FIG. 1) to communicate with the camera 114. When the inspector begins taking pictures, any pictures taken are wirelessly transmitted to the portable computing device, and incorporated into the open inspection form for that particular inspection. These photos will ultimately be saved along with the answers made regarding that particular asset. If a thickness-measuring device (e.g., ultrasound device 113) is used along with the system (see FIG. 1), a separate on/off Bluetooth enabling button could be offered. Thickness readings taken after hitting the Bluetooth enabling button will be automatically saved along with the form for that inspection like with the photo functionality. Thus, the photos and/or thickness readings taken will be automatically associated with (and ultimately saved with) the particular inspection for which the form is open on the handheld computer 112.

Once: (i) all the questions have been answered; (ii) photographs taken; and (iii) thickness readings recorded for that particular inspection item, the inspector saves the information locally. The taking of photographs, and/or, the taking of thickness readings are totally optional processes, and not required before making a local save of the inspection. Answering of the question is, however, required before the save of the inspection is allowed. This prevents the inspector from forgetting to answer questions, and having to return to the asset to obtain information.

Once the local save occurs, the inspector then moves to the physical location of the next asset to be inspected (after locating it on the map). Selecting from the inspection map and lists, the inspector opens up the form (by making a map click or finding asset on list) for the next asset to be inspected. Once the form for the new asset is opened up, any photos or readings taken will be automatically associated with it.

This process is repeated until a desired number of the inspections in the work order/inspection have been completed. The list could be totally or partially completed before upload (which requires internet connectivity).

At any time, the inspector can add assets and inspections on an ad hoc basis. To do this, the inspector can click on an "add inspection" button on map page. This brings up a full screen map which can be marked up. The inspector can doodle on this map (e.g., circle the asset location for the new inspection) and this brings up a blank form with no pre-population. The inspector then fills in the blanks, for example, possibly a passive fire protection (PFP) type and other specifications relating to the asset in question. The same listed questions are presented based on the PFP type.

The inspector cannot add questions. Questions must be developed by the inspection facilitator (and then possibly approved by the site owner administrator). This avoids inconsistencies over time.

Then the inspector, once access to the internet 102 is available through wireless or a wired connection, uploads all the inspection results onto the website.

Once uploaded, the inspection data obtained on site is used to make condition rankings, cost formulations, create a repair plan, and also used to create the dashboard. The inspection is also archived for future use. The ad hoc questions or assets added by the inspector are considered by the administrator, but not added permanently without acceptance by the facility administrator. These processes are in place so that the questions are uniform from year to year.

Future work orders can be created by the inspectors themselves using the web application and the questions from the earlier year since all the specification fields will have already been filled in (e.g., measurements, etc.). Any changes needed because of equipment updating (new vessel, etc.) will be handled using the add asset and inspection feature discussed above.

The System

The system components used in one embodiment 100 for the inspection tool are shown in FIG. 1. Referring to the figure, it can be seen that the many components exist in a network 102 of some sort, e.g., a wireless network, the internet, an intranet arrangement, or a combination of these or other networks. The web application discussed hereinafter runs on one or more web servers 104. The web server 104 shown in FIG. 1 is supported by a data server 106 which is used to manage an archiving database 108. A site owner's computing device 110 can be used to access the web application running on server 104, and execute set up operations, push inspection requests to inspectors, and perform other functions. This computing device 110 (or a group thereof) will likely exist at the company requesting the inspections.

The inspectors in the field will use a variety of portable devices. One could be a handheld computing device 112, e.g., an iPad®, other smart tablet, smart phone, or some other computing device, portable or not, on which a local application will run. This handheld computing device 112 (shown in FIG. 1 as being on location at an inspection site 115) will interface with a digital camera 114 which includes a content-aware digital media card 116 which has wireless capabilities. The computing device 112 will also be able to, in embodiments, wirelessly communicate with a wirelessly enabled thickness measurement device 113.

In one embodiment, card 116 includes a camera interface, memory component for temporary photo storage, a logic module for interacting between the camera interface and memory, and a transceiver which relates between the logic module and a Wi-Fi antenna. In one embodiment, the card 116 is Wi-Fi capable, and enables the camera to interface with and also download pictures to the handheld device 112. An example of the sort of special card 116 is the product referred to as an Eye-Fi® card marketed by Eye-Fi, Inc. located in Mountain View, Calif. The Eye-Fi® card actually creates a Wi-Fi hot-spot, and is able to interface with another wireless device if that device is configured to transmit a signal including a unique key number that the card 116 is designed to recognize.

A thickness measurement device 113 is optionally included along with the system. In one embodiment, an Elcometer 456 device manufactured by Elcometer, Inc. located in Rochester Hills, Mich. is used as the thickness measurement device 113. This sort of device is capable of wirelessly interfacing with the handheld computing device 112. Thickness measurement devices—like the Elcometer 456—use ultrasound technologies to do the measuring. Then Bluetooth® technologies are used to transmit the thickness readings taken from the device 113 to the portable computer 112.

An inspection facilitator 122 (e.g., a company dedicated to facilitating asset inspections) primarily controls the operations of the web-based backend arrangement 124 (comprising the web server 104, data server 106, and archiving database 108) using one or more computing devices 120 possessed by facilitator 122. Site owner 118 is able to access the web-based systems 124 to use the website, and in some embodiments, given limited controls (using one or more computing devices 110).

The inspector in the field (using portable computing device 112), in an embodiment, is given no direct control over the web applications running on server 104, but can access the website. The inspection facilitator 122 maintains primary control over the web systems 124 so that there can be uniformity in the inspection process.

Set Up Processes

Create Inspection

Inspection facilitator 122, normally at the direction of a site owner administrator 118, creates a full electronic inspection, which will include maps, assets to be inspected, and other information provided. The facilitator 122 can use any computer having access to the web 102, e.g., local computer 122, to create an inspection. This is done by interfacing over the web with the web-based system 124 by interfacing with the application running on server 104.

Create Map

To create the maps which will be used in the inspection process, the inspection facilitator 122 will normally receive existing site information, e.g., plan drawings, asset lists, schematics, etc. regarding a customer site 115 from the site owner 118. The schematics can be transmitted from a computing device 110 controlled by site owner administrator 118 over network 102, or otherwise transmitted from the site owner administrator 118 to the facilitator 122. The map will typically be created on the backend system 124 over the web using any computer on the web, e.g., computer 120, to interface with the web server 104 and establish the maps on the database 108. These maps are then made available to the processes running on web server 104. The schematics, in some instances can be used as they exist electronically, but in other instances they must be wholly or partially electronically regenerated by the facilitator 122. Regardless, an acceptable electronic version will be made available to the web application operating on server 104.

In some cases, multi level maps will be helpful. For example, on a first level the map could be for an entire facility, e.g., a plant, and sub-portions (e.g., particular processing stations) included in this comprehensive map can be made selectable. Upon selection of a sub-portion, greater details regarding that sub-portion can be made visible (e.g., vessels, structural components, etc.). Really any number of tiers/levels of web page depth could be offered and still fall within the scope of the disclosures herein.

In addition to this tiering of maps, the facilitator 122 might want to include different kinds of maps to further facilitate the identification process in field inspections. For example, any of plan drawings, sky views, or even three dimensional drawings could be offered. In an embodiment, all three are offered as alternative drawings.

Number Assets

Next, the facilitator 122 on computing device 120, or by interfacing with the web application operating on server 104, associates each item to be inspected in the site (e.g., items associated with assets in a plant) with a unique identifier. In some embodiments, these unique identifiers will be created according to a numbering scheme.

In some embodiments, an inspection item number hierarchy can be created. For example, where an asset component (e.g., a vessel) includes numerous subcomponents (e.g., pipings, shell, skirt courses), the generic asset can be given a classification number identifier (e.g., "VOOO2") and the subclass components can each be given sub-identifiers (e.g., shell="VOOO2-001"; skirt course="V0002-002"). This enables an elaborate inspection identification system in which the items can be listed in a numbered sequence, and classified. In an embodiment, the inspection facilitator 122 lists the more general components as classifications in sequence, and the sub-identifiers as subclasses immediately underneath the components they are a part of.

Match Assets with Points on Map

Next, facilitator 122 creates clickable points on the electronic versions of the maps (e.g., schematics, plan drawings, sky view photographs, 3-D representations), each point being at a location of an inspection identifier (e.g., number). Where an elaborate hierarchical numbering scheme is used (as discussed in last paragraph), the generic identifier (e.g., representing Vessel "V0002") can be plotted on the map, and the subcomponent shell identifier "V0002-001" and skirt course identifier "V0002-002" brought up when the generic asset is clicked on. All of this results in an interactive map in which clicking on a high level identifier in a location brings up one or more a fillable report screens related to more specific features. These screens will all relate to the numbered components and subcomponents, and will enable the inspector to input answers to inspection questions posed.

Standardized Question Creation

This question scheme, in embodiments, is primarily created and then controlled by the inspection facilitator 122 using the web-based system 124. In terms of creating the questions, sets for each inspection item can be initially posed by facilitator 122. In embodiments, the site owner administrator will have the ability to suggest and approve the questions. Facilitator, however, provides the tremendous benefit by creating standardized questions which will be repeated year after year, and will not be subject to deviations and customizations engaged in by the independent inspectors. Although the inspectors can add inspection items in the field, the questions will not be changeable by the inspector in the field or anyone else besides the facilitator 122 to maintain consistency. The site owner administrator 118 will, in embodiments, will of course want to ensure that the questions incorporated are sufficient to ensure safety and satisfy relevant regulations, but most of the burdens relating to the inspection process are borne by the facilitator 122 using the web-based system 124.

Later, these questions will be included in a fillable inspection report which will be downloaded by an inspector operating the portable computing device 112. But again, the inspector will not have the ability to directly change any of the questions asked. In embodiments, the on-site inspector is given the ability to suggest additional questions, add questions, or include additional comments. But because the inspector cannot change them without approval, the site owner administrator 118 can maintain them in a standard form from one inspection to the next.

Operation

Figure 2:
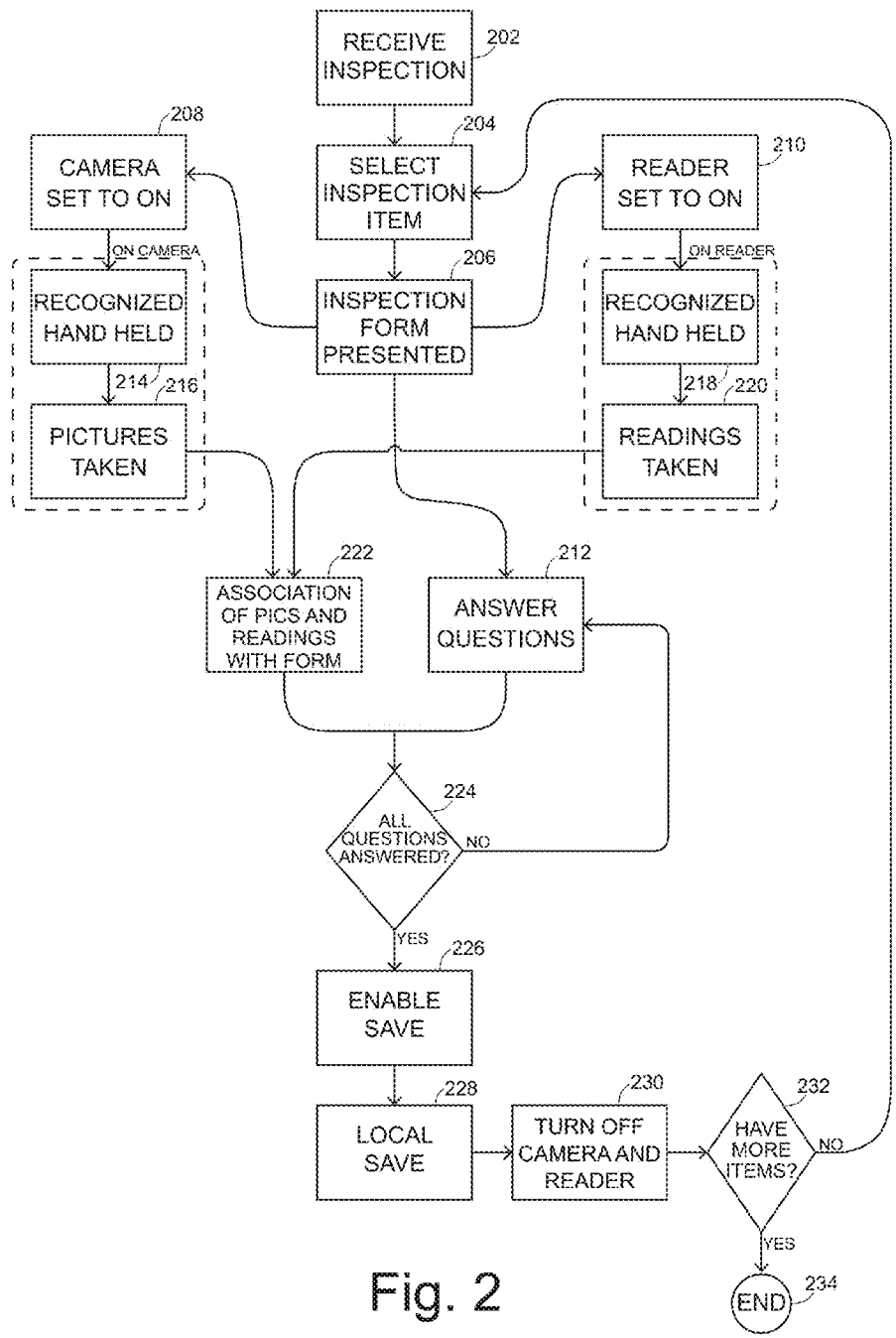
FIG. 2 illustrates a process flow diagram showing the operations of the local application operating on an inspector's handheld or other computing device for one embodiment of the processes of the inspection tool of the present invention.
Figure 3:
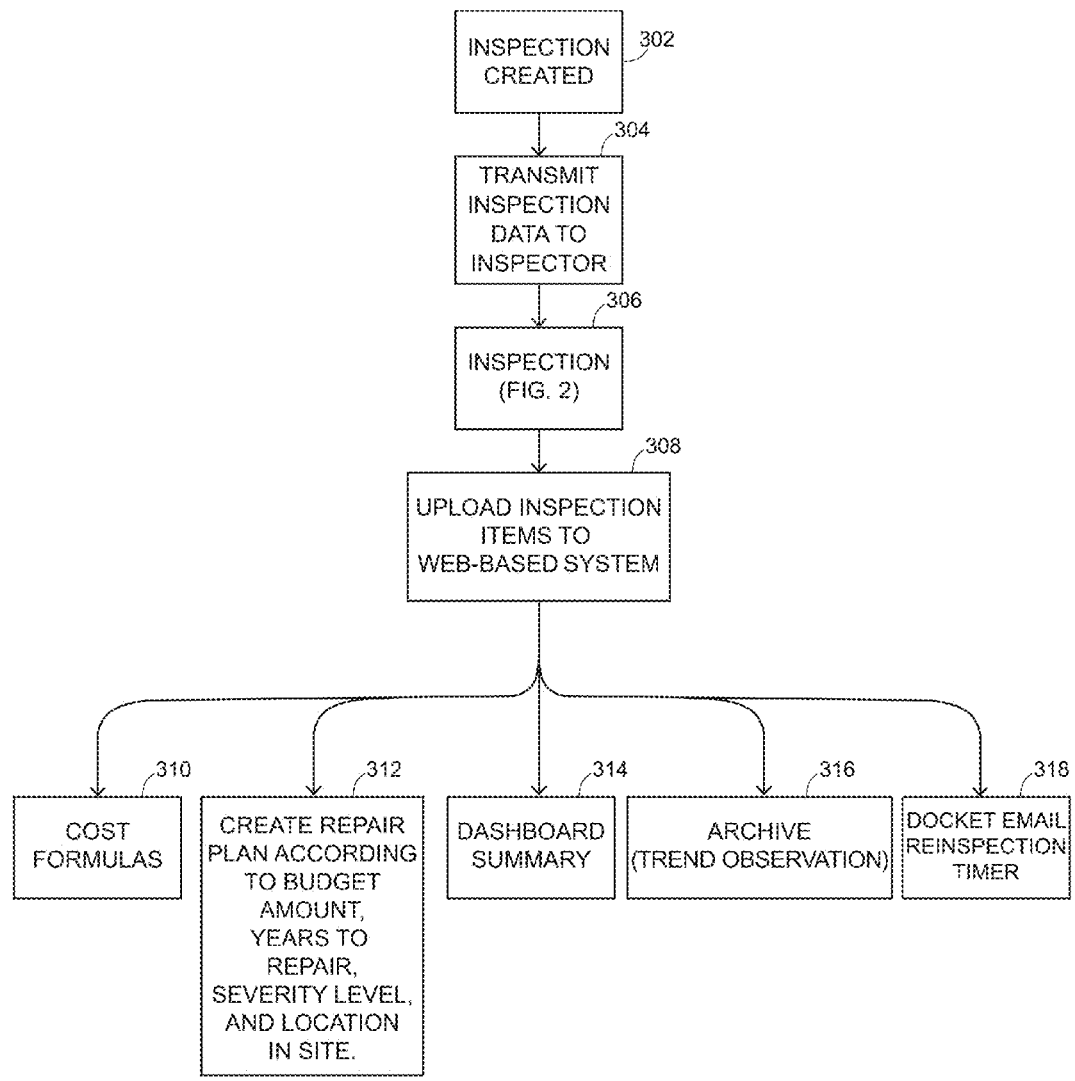
FIG. 3 illustrates a process flow diagram showing the steps executed in a web application for one embodiment of the inspection tool.

The operations of the inspection tool are shown in two perspectives in the figures. FIG. 2 discloses the processes from the perspective of the local application operating on the handheld device 112 at the inspection site 115. FIG. 3 illustrates the processes from the perspective of the web application operating on the web server 104.

As a preliminary, in a step 302 (see FIG. 3) the inspection (a/k/a "work order") is created. This will normally initially be requested by the site owner administrator 118. This will likely involve administrator 118 forwarding information necessary to create the inspection (e.g., maps, asset information) regarding a site, e.g., site 115. The facilitator 122 then creates the inspection on the web-based system 124 as discussed above. The inspection, after it has been prepared by facilitator 122, is then maintained on database 108. (See "Create Inspection" above underneath the "Set Up" heading).

Next, in step 304 of FIG. 3, an inspector in the field may request the inspection using the website 124. Alternatively, the site owner 118 or facilitator 122 can request (by interfacing with the web application operating on web server 104) that the inspection be transmitted to the hand held computing device 112 over the internet 102. The data transmitted will include the questions regarding the assets to be inspected, a number of parameters (e.g., dimensions of asset components) which will be the same from inspection to inspection, and also the map information relevant to the inspection.

Once the inspection has been transmitted to the hand held device 112, the inspector can take the hand held device 112 to site 115 to conduct the inspection. Site 115 could be an oil rig derrick, refinery, or any other site which requires periodic inspections due to safety or other reasons. Access to the internet 102, e.g., a wireless or hard-wired connection, will not be necessary to conduct the inspection at site 115. The local application operating on the hand held, along with— optionally—the camera 114 and reader 113 will be enough to gather the necessary inspection data.

In FIG. 3, the actual inspection at the site (where the inspection items will be examined) is identified as step 306. The details of this step are seen in FIG. 2. In a first step 202 in the FIG. 2 process, the electronic inspection is received into the handheld 112. The inspector, now at the site 115, will open up the local application operating on handheld 112, e.g., an iPad®. This will result in the inspector being presented with the inspection-item reflecting maps and lists discussed already above.

Selecting Assets from Maps or Lists

Figure 4:
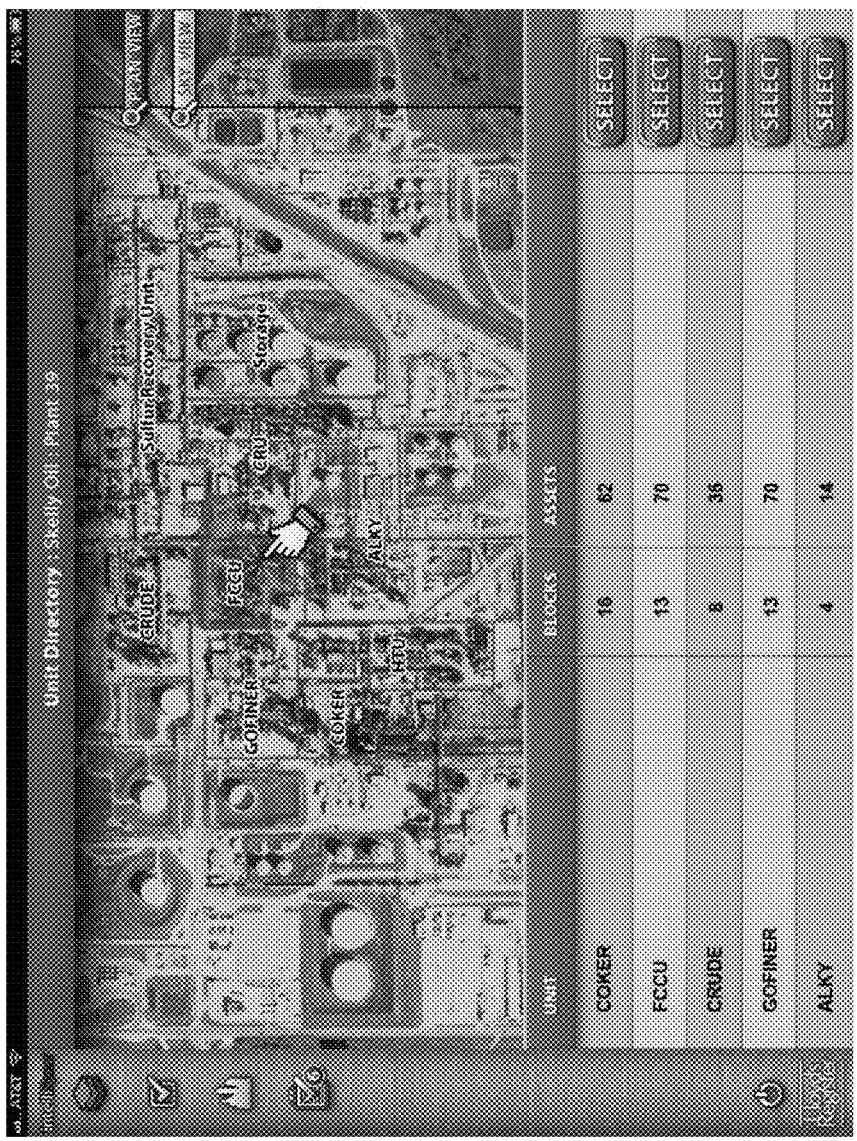
FIGS. 4-11 show embodiments of computer generated interfaces useable for receiving and displaying information in accomplishing the processes of the disclosed methods.

In step 204, a particular inpection item is selected. For example, the selections can be made from the numbered lists, or asset points created in various maps, e.g. plats, schematics, sky-view photographs, 3-D renderings. As can be seen in FIG. 4, which is a sky view map, a click on a portion of a plant ("FCCU") when clicked on (see figure) brings up the more specific 3-D rendering of FIG. 5 which discloses an asset point, "0136", which when clicked (see figure) will bring up the library shown in FIG. 6. The lists generated, in embodiments, are organized sequentially by the identifiers referred to in the Set Up section above. The inspection item asset points also display the identifiers discussed above.

Figure 5:
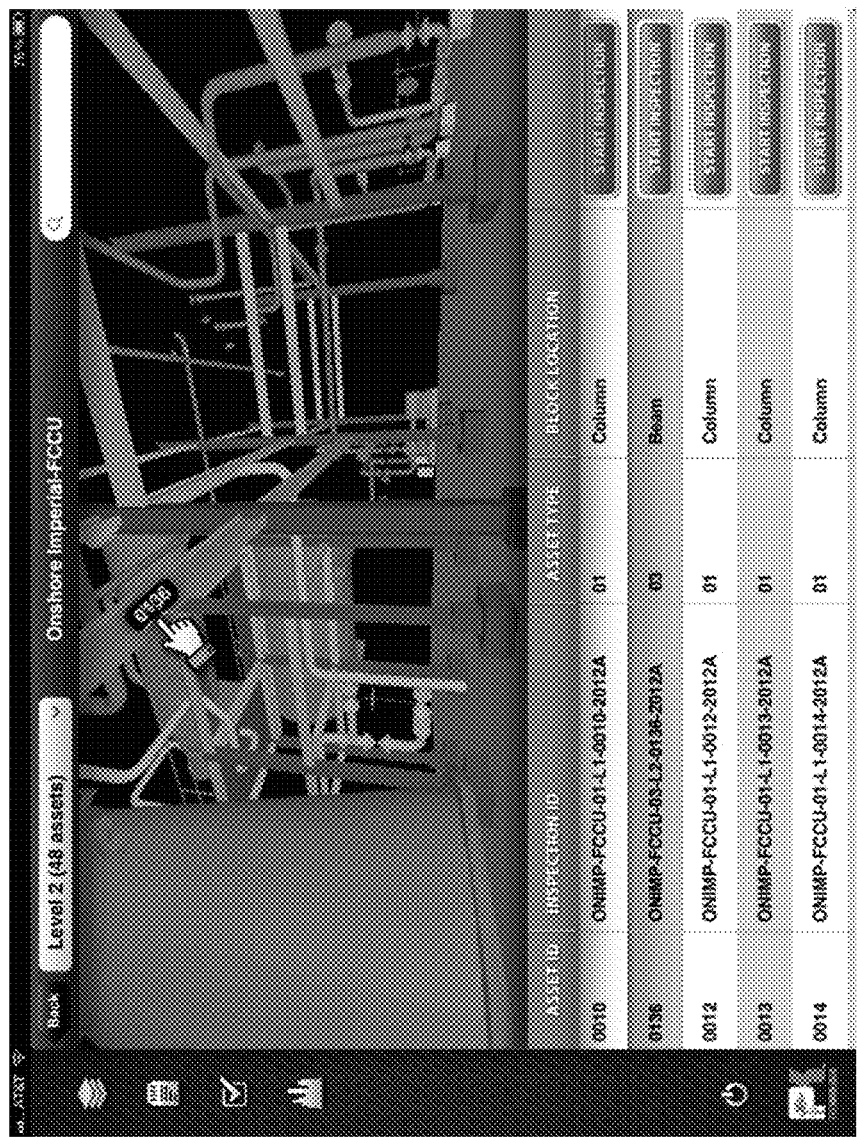
Figure 6:
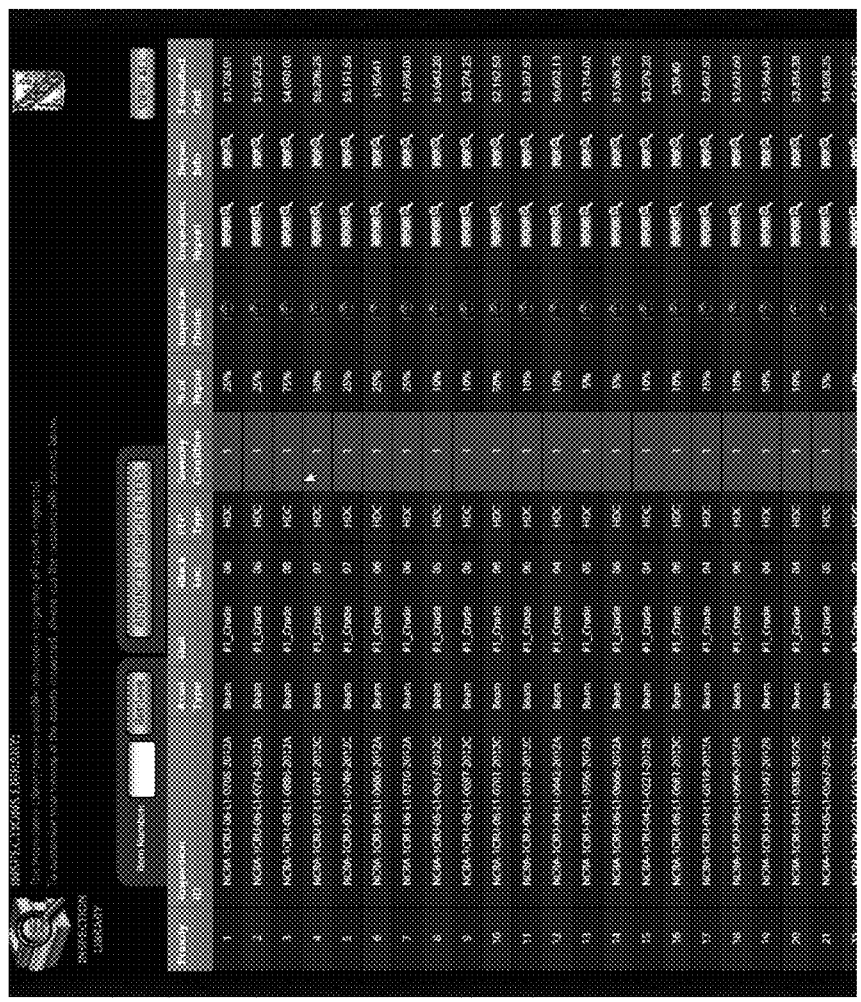
Figure 7:
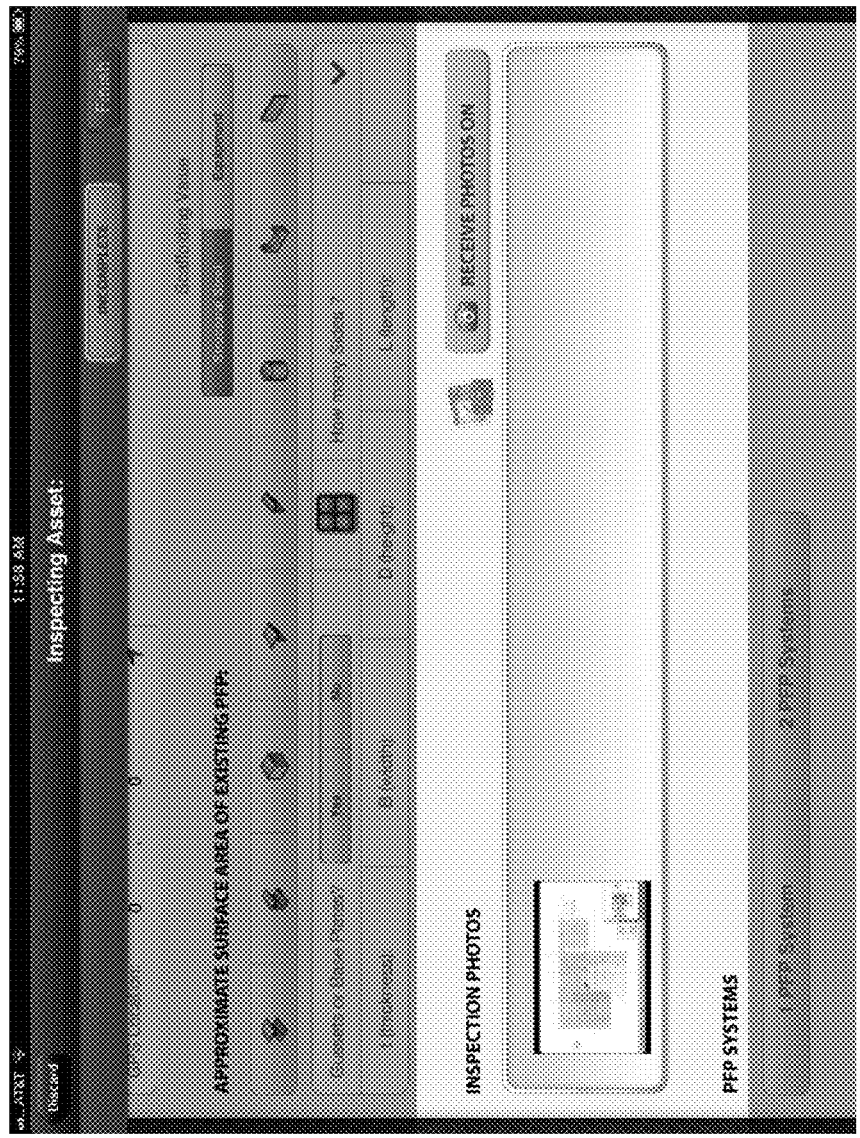

The inspection library (see FIG. 6) on the hand held device 112 includes list of assets and associated hyperlinks. Clicking on either a listed inspection item, or alternatively, directly from a mapped inspection-item asset point (see FIG. 5, "Start Inspection"), will, in step 206, bring up the inspection form (see, e.g., FIG. 7) for that particular inspection item. Again, each inspection item has an identifier, e.g., a particular number. Referring to FIG. 5, the top-listed identifier is "ONIMP-FCCU-01-L1-0010-2012A," and other identifiers are listed below that. Each of these identifiers, when selected by hitting the "Start Inspection" field, will be used to bring up the form (see FIG. 7) devoted to that particular inspection item.

In a second map-driven embodiment, a site map is presented after the site selection is made by the inspector. The inspector visually locates the inspection item location points on the map, and that brings up zones which when selected, reveal sub maps on which asset lists are generated. These sub maps are created to be viewable in either plan view (displaying engineering illustrations), a sky view (using actual photographically generated maps), or even in a three dimensional view. Inspection item point labels (with associated hyperlinks) are included into the drawings to identify the particular asset depicted in either the plan view, sky view, or three-dimensional options presented. The application is configured such that the selection of an inspection item from the map point will bring up the relevant inspection item, the selection of any particular item then bringing up a fillable inspection form relating to the item selected.

Those skilled in the art will recognize that numerous known techniques for classification, listings, and mapping components could be used singly or in combination to achieve the objectives of allowing for the selection of numbered inspection items in step 204 such that a form for the selected item is then brought up in step 206. The form and other information relating to the inspection item are all displayed on the hand held device 112.

Along with the form, one or more on/off buttons are also displayed. One button provides the user with the means for enabling the wireless receipt of photos from the digital camera 114. In one embodiment, this icon enabling the turning on and off is shown as the image of a camera. Activation of the camera button (in a step 208) thus enables the inspector's use of the wireless camera to take photos to go along with the inspection form. A reader on/off button is also offered. Like with the button for the camera, activation of the reader on/off button (in a step 210) results in the handheld 112 being able to receive Bluetooth® transmitted depth readings and incorporate them into and along with the electronic form. In a step 212, the inspector answers the standardized questions posed in the inspection form presented on the hand-held device 112. The answering can be done through a combination of drop-down selections from menus, the population of designated fields, or other techniques of gathering information.

Photo and Reading Incorporation into Inspection Form

At the same time the questions are being answered, at any time the inspector activates the camera icon (in a step 208), he or she may also elect to take digital photos to show a condition of an asset, or a part of an asset. These photos will be automatically received into the hand-held device, and incorporated into the form for the particular asset being evaluated. Processes running on the hand-held device 112, when the camera icon is clicked on (see "Receive Photos On" button in FIG. 7), cause a signal to be transmitted. The signal includes the particular key that is recognized by the wireless card 116 in the digital camera 114. Once the content-aware wireless card 116 recognizes the signal, and thus the handheld in a step 214, the card 116 includes logic which causes any photographs taken in a step 216 to be immediately transmitted to the handheld device 112 which is also wirelessly enabled. It should be noted that steps 214 and 216 occur on the digital camera using the card 116.

In another parallel process, the selection form screen also includes an icon that when turned on in a step 210 allows a thickness reading device 113 to be recognized by the handheld computer 112. See step 218 in FIG. 2. Thereafter, any readings taken by device 112 (see step 220 in FIG. 2) will be automatically displayed along with the answers to the inspection questions.

As the inspection process proceeds, the pictures and readings taken in steps 216 and 220 are associated (in a step 222) with the form for the inspection being done on that inspection item.

The form, in embodiments, includes a "save" button. But a save is only enabled (in a step 226) if all of the inspection questions have been answered with respect to that particular inspection item. That the form is able to be saved is indicated (in embodiments) by the save button being highlighted.

When the local save 228 is executed, the form is closed, and a next step 230 automatically turns of the camera and thickness reader settings so that further photos and/or thickness readings will not be able to be associated with that particular inspection item.

It should be noted that in an alternative embodiment, handheld device 112 alone could be used to take the pictures. It is widely known that numerous handheld smart devices (e.g., laptop computers, smart phones, and smart tablets) all have onboard cameras. Thus, in some embodiments, this already-incorporated camera could be used instead of, or in addition to digital camera 114. Like with the earlier embodiments, the form screen would include a separate button devoted to turning the onboard camera on or off. Once turned on, any photos taken using the onboard camera would automatically be incorporated into the particular inspection-item form which happened to be opened up at that time. And like with the already mentioned embodiments, when step 230 is reached, the onboard camera would be automatically turned off so that further photos taken would not be associated with the inspection form currently being saved.

In a next step 232 the inspector determines if any further inspection items exist that have not yet been completed. If so, then the process returns to step 204 where the inspector selects another inspection item to inspect. If not, then the process ends as shown. It should be noted that the inspector does not have to complete all the inspection items in a single day.

Figure 8:
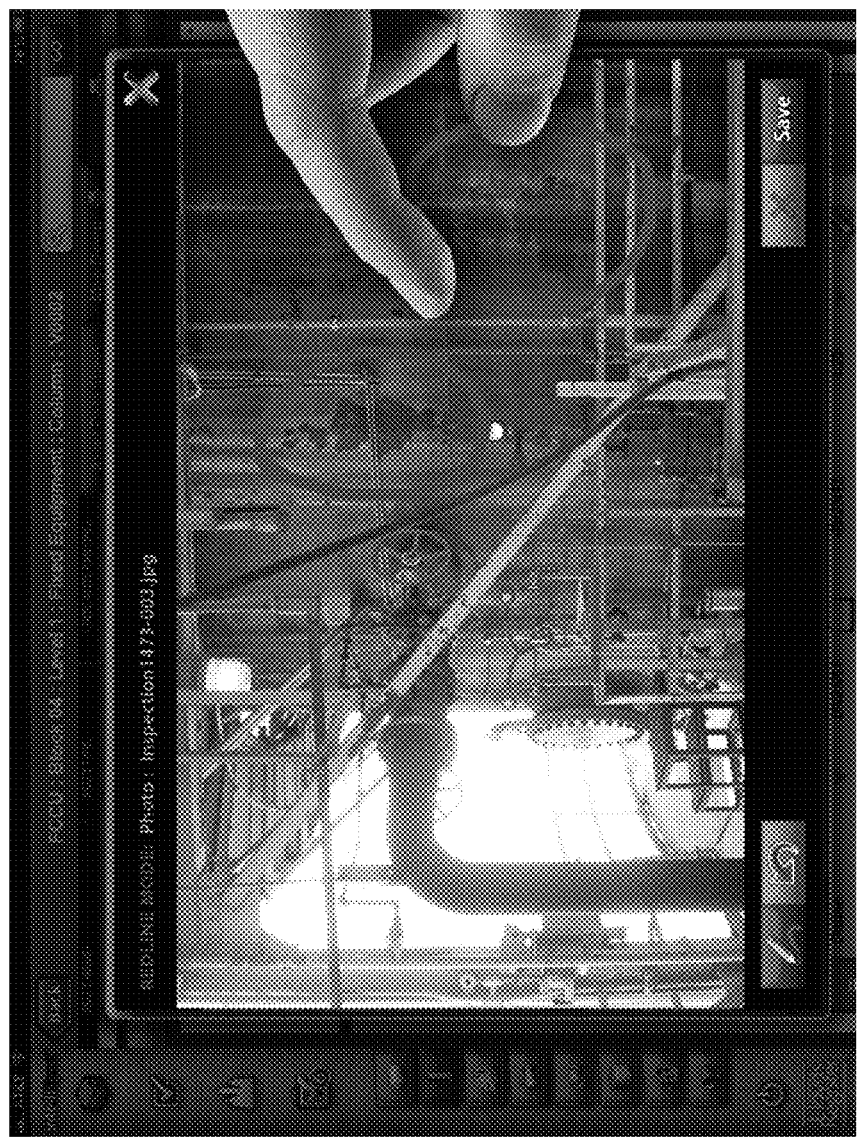
Figure 9:
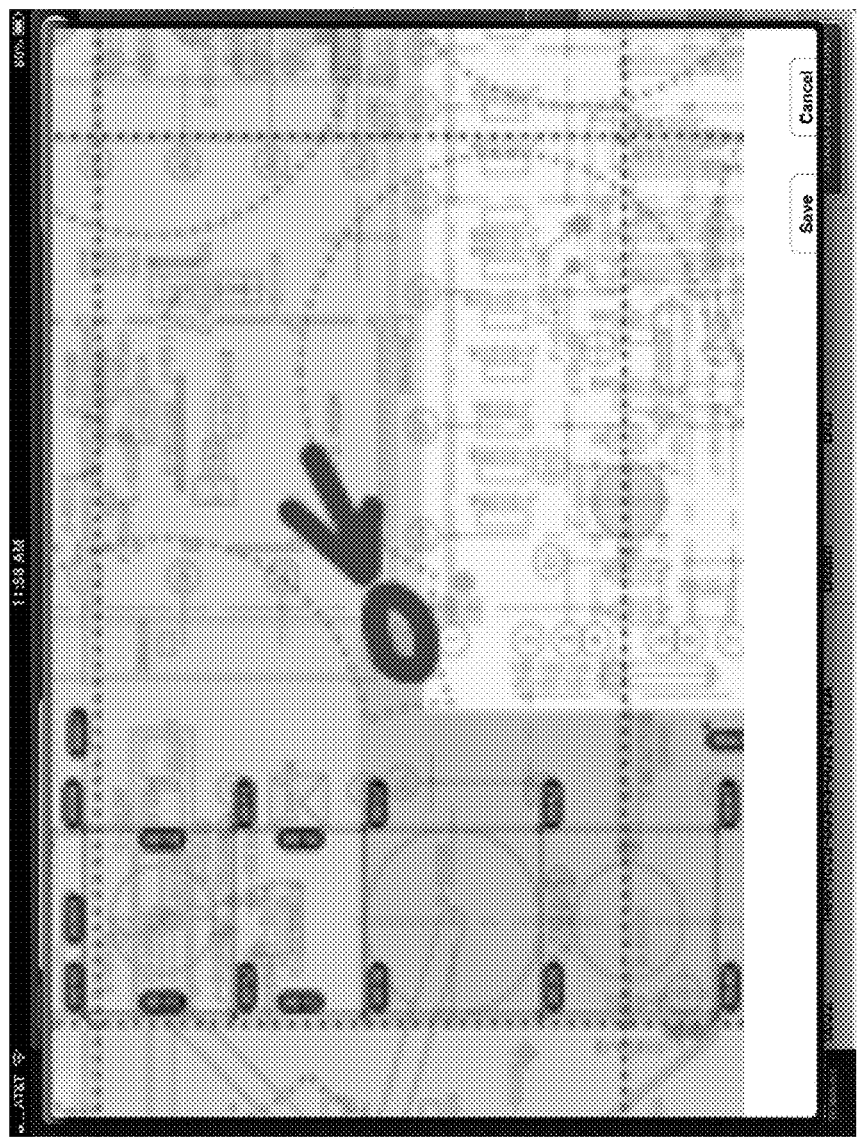

At any time during the inspection process, the inspector can add assets and inspections on an ad hoc basis (not reflected in FIG. 2). To do this, the inspector can click on an "add inspection" button on map page. This brings up a full screen map which can be marked up. (FIG. 8 shows an interactive 3-D map, and FIG. 9 shows a markable plan drawing where add on items can be circled and arrowed). The inspector can doodle on the map (e.g., circle the asset location for the new inspection) and then brings up a blank form with no pre-population. The inspector then fills in the blanks, for example, possibly a passive fire protection (PFP) type and other specifications relating to the asset in question. The same listed questions are presented based on the PFP type.

The inspector cannot add questions. Questions must be developed by the inspection facilitator (and then possibly approved by the site owner administrator). This avoids inconsistencies over time.

Moving back to the processes disclosed in FIG. 3, it can be seen that once the inspector is able to make an internet connection (either wired or wireless) he or she can (in a step 308) upload the locally saved inspection data recorded to the website. This uploading can occur regardless of whether all the items in the particular work order have been inspected or not. For example, many inspections will take days to complete. In such cases, it might make sense for the inspector to upload the inspection data every day so that the inspection facilitator can continually monitor work order status.

The uploaded data is then utilized by the web application (running on server 104) and used for many useful purposes.

Cost/Budget Estimator

Another process executed by the website 124 is in a step 310 estimates costs. More specifically, the process uses the inspector's answers to the standardized questions as inputs into cost formulas and projects cost. For example, in embodiments (i) square footage of surfaces needing repairs, (ii) difficulty in obtaining access to the asset, e.g., need for scaffolding, (iii) permits required to do the work on the asset, and/or (iv) the habitat required for doing the work are received as inputs into formulas by which costs are estimated on an asset-by-asset basis. Also, total costs for bringing the site into compliance can be determined, in that a total cost tally can be computed, allowing the user to maintain costs below certain levels, and then, based on the severity level determinations made in step 312 (discussed below), make repair determinations by comparing budget against cost cut offs based on severity level.

Repair Plans/Prioritization Matrix to Determine Severity Levels

Figure 10:
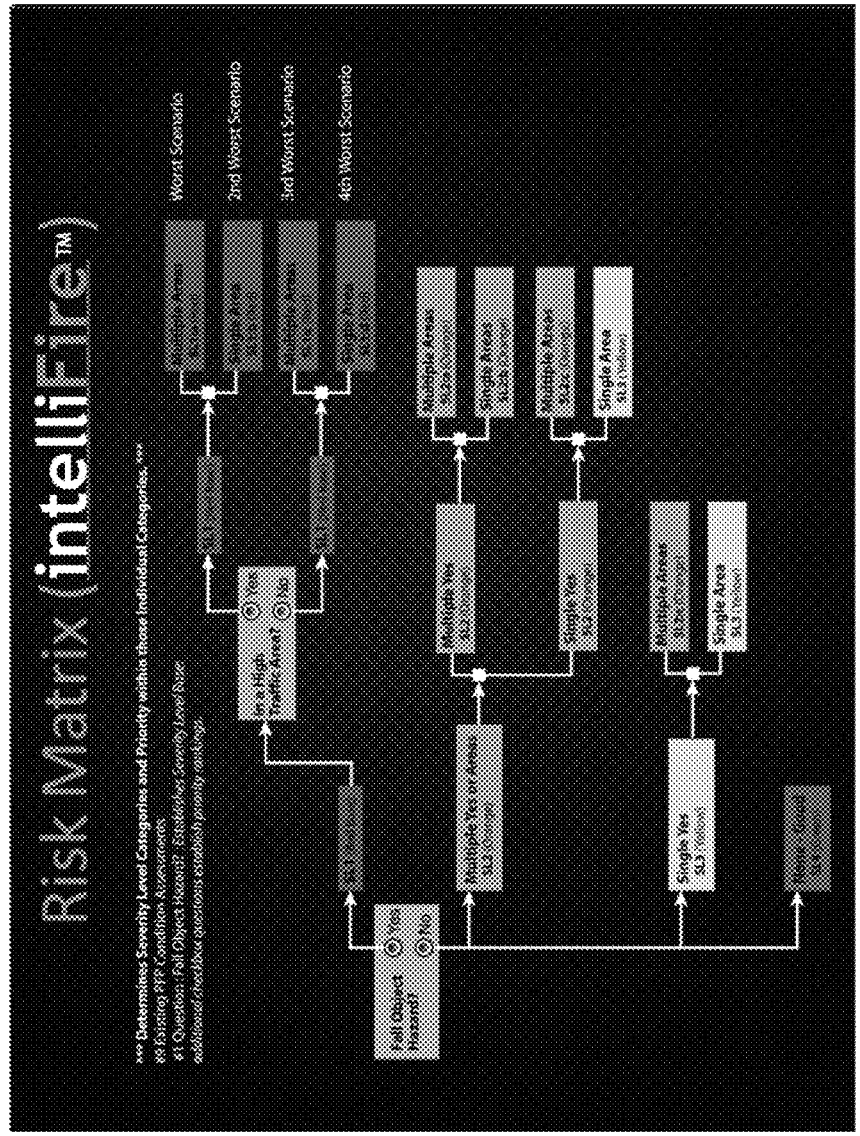

The first of these simultaneous processes is step 312, where the local application running on hand-held 112 receives the inspector's answers to questions posed in step 212, and uses decision tree to reach a conclusion regarding how important correction may be in order to avoid the asset being a hazard. For example, the decision tree of FIG. 10 demonstrates how the answers to questions results in a severity level ranking. Referring to the figure, it can be seen that an asset that is a fall hazard, is in a high traffic area, and has degradation issues in "multiple areas" gets a Severity Level 1 ("SL1") "worst Scenario" ranking. (See ranking in step 222). In the disclosed embodiment, this ranking will situate the particular asset against the others in order of severity level on a list that is updated as the assets are being evaluated. In embodiments, the different severity levels can be color coded.

By addressing the asset conditions by severity level, the application will be able to sort the assets top to bottom in terms of need for repair (based on severity level). An example of a list generated is shown by referring back to FIG. 6. Referring to the figure, it can be seen that under the "Severity Condition" column, the top listed assets in terms of severity are shown as ones. It should be understood that a continuation of the page downward would result in the ranking reaching "2's" and "3's" and so on. A repair plan can also be created using the established ranking of repairs by creating cost cut offs by ranking, and using other methods.

Dashboard Summaries

Figure 11:

In another step 312, a process on server 104 creates a dashboard summary which will be made available to those accessing the inspection over the network 102. As can be seen in FIG. 11, the summary may include and highlight numerous high-level inspection results of interest, e.g., risk assessments, cost estimates, inspection progress, etc.

Archiving and Trend Monitoring

The saved inspection report, is thus archived (see step 310), and will now be available to the client 112, site owner administrator 118, inspection facilitator 122, and any other authorized parties accessing database 108 over the internet 102.

Because the questions remain the same from inspection to inspection, persons accessing archived inspections done in past years are able to see changes in asset condition, e.g., degradation, over time.

Reinspection Docketing

The web application also allows the inspector to schedule a future series of inspections relating to the work order just completed. Future inspections will not require the burdensome inspection creation step 302 because the maps and asset information (e.g., inspection item unique identifications) will already be in the system. Thus, the inspector can initiate the next inspection using the archived information.

Unless otherwise specified, any terms used herein should be interpreted broadly and liberally to the extent allowed by the art and the meaning of the words offered in context.

As one skilled in the art will appreciate, the present invention may be embodied as, among other things: a method, system, or computer-program product. Accordingly, the present invention may take the form of a hardware embodiment, a software embodiment, or an embodiment combining software and hardware. In a preferred embodiment, the present invention takes the form of a computer-program product that includes computer-useable instructions embodied on a computer-readable medium.

Computer-readable media include both volatile and nonvolatile media, removable and nonremovable media, and contemplates media readable by a database, a switch, and various other network devices. Network switches, routers, and related components are conventional in nature, as are means of communicating with the same. By way of example, and not limitation, computer-readable media comprise computer-storage media and communications media.

Computer-storage media, or machine-readable media, include media implemented in any method or technology for storing information. Examples of stored information include computer-useable instructions, data structures, program modules, and other data representations. Computer-storage media include, but are not limited to RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These memory components can store data momentarily, temporarily, or permanently.

Communications media typically store computer-useable instructions—including data structures and program modules—in a modulated data signal. The term "modulated data signal" refers to a propagated signal that has one or more of its characteristics set or changed to encode information in the signal. An exemplary modulated data signal includes a carrier wave or other transport mechanism. Communications media include any information-delivery media. By way of example but not limitation, communications media include wired media, such as a wired network or direct-wired connection, and wireless media such as acoustic, infrared, radio, microwave, spread-spectrum, and other wireless media technologies. Combinations of the above are included within the scope of computer-readable media.

The processes (methods) and systems, including components thereof, herein have been described with exemplary reference to specific hardware and software. The processes (methods) have been described as exemplary, whereby specific steps and their order can be omitted and/or changed by persons of ordinary skill in the art to reduce these embodiments to practice without undue experimentation. The processes (methods) and systems have been described in a manner sufficient to enable persons of ordinary skill in the art to readily adapt other hardware and software as may be needed to reduce any of the embodiments to practice without undue experimentation and using conventional techniques.

While preferred embodiments of the disclosed subject matter have been described, so as to enable one of skill in the art to practice the disclosed subject matter, the preceding description is intended to be exemplary only. It should not be used to limit the scope of the disclosure, which should be determined by reference to the following claims.

The present invention has been described in relation to particular embodiments, which are intended in all respects to be illustrative rather than restrictive. Alternative embodiments will become apparent to those skilled in the art that do not depart from its scope. Many alternative embodiments exist but are not included because of the nature of this invention. A skilled programmer may develop alternative means of implementing the aforementioned improvements without departing from the scope of the present invention.

It will also be understood that certain features and sub-combinations are of utility and may be employed without reference to other features and subcombinations and are contemplated within the scope of the claims. Not all steps listed in the various figures need be carried out in the specific order described.

I claim:

1. A tool for conducting inspections, the tool comprising:
   an inspection-item presenting process operating on a hand held computing device, the inspection-item presentation process causing the display of a map showing a plurality of assets, the selection of an asset bringing up a list of selectable inspection items related to the asset, each inspection item being associated with an identifier, wherein the map is at least one of a plan view, sky view and 3-dimensional rendering of a facility and wherein each of the plurality of assets are represented on the map according to a corresponding physical location of each of the plurality of assets in the facility;
   an information-gathering process also initiated upon the selection of a particular inspection item having a particular identifier, the information-gathering process opening up an inspection form for the particular item selected on the hand held computing device, the form posing standardized questions relating to at least one condition relating to a fire-protection coating existing on the particular asset, the standardized questions made to be unalterable by a user of the handheld device;
   a camera-interfacing process which is turned on by the user by interfacing with the hand held computing device, the camera-interfacing process causing a signal to be transmitted by the handheld computing device, the signal enabling interfacing with, and downloading photos from a camera;
   a photo-association process which, after the camera-interfacing process is turned on, automatically incorporates at least one photo taken using the camera into the inspection form, associates the photo with the particular identifier;
   the photo-association process automatically terminating when the user closes the form on the hand-held device so that a subsequently taken photo will be associated with a subsequent identifier; and
   a coating thickness-reading-device-interfacing process enabling the handheld to download thickness readings into the inspection form by directly interfacing with a thickness reading device which determines thickness by sending and receiving waves to determine coating depth.

2. The tool of claim 1 wherein the camera-interfacing process further comprises:
   wirelessly transmitting the signal to a wirelessly-enabled digital camera separate from the hand-held computing device to enable wireless downloading from the camera of the photo into the inspection form.

3. The tool of claim 1 wherein the camera-interfacing process further comprises:
   the photo being received from an on-board camera located physically on the handheld into the inspection form after the on-board camera is turned on.

4. The tool of claim 1 comprising:
   a close-out step wherein upon the completion and saving of the inspection form, the downloading of photos from the wirelessly-enabled camera into the form is terminated with respect to any subsequently taken photos.

5. The tool of claim 1 comprising:
   a set-up process which includes creating a group of standardized questions for the inspection item, the group of standardized questions repeated for inspection items of the same type, as well as in subsequent inspections for the inspection item;
   assigning a unique identifier for each inspection item such that a form for that item, the standardized questions posed, any photos taken, and any answers to the questions will be associated with the unique identifier.

6. The tool of claim 5 comprising:
   a prepopulation process wherein some already-known parameters regarding the inspection item are included into the form before the form is presented to the inspector.

7. The tool of claim 6 comprising:
   including the size of an inspection item into the form as a part of the prepopulation process.

8. The tool of claim 1 wherein the thickness-reading-device-interfacing process automatically incorporates a thickness reading made using the thickness reading device into the inspection form.

9. The tool of claim 1 comprising:
   an inspection-completion-assurance process requiring an inspector to answer all of the standardized questions posed for the particular inspection item before the form can be saved.

10. The tool of claim 1 comprising
    a web-based risk-prioritization process wherein upon receipt of a plurality of answers to the standardized questions posed from the handheld is used to navigate a decision tree to reach a ranking in order of need for repair of the inspection items.

11. The tool of claim 10 wherein the risk-prioritization process comprises:
    a cost-projection process wherein a plurality of answers to the standardized questions posed are accepted as inputs into cost formulas to project costs; and
    a cost cut off process wherein a predetermined budget is applied to a higher-ranked group of inspection items and denied to a lower-ranked group of inspection items, and the higher-ranked group is recommended for payment.

12. The tool of claim 1 wherein the coating thickness-reading-device-interfacing process which is activated by a user by changing a setting on the hand held.

13. The tool of claim 1 comprising:
    both of the camera interfacing and coating thickness reading processes being executed by directly interfacing with the handheld and without the need for access to a wide area network.

14. The tool of claim 13 wherein Bluetooth® is used to execute both the camera interfacing and coating thickness reading processes.

15. The tool of claim 1 wherein ultrasound is used to determine thickness.

16. An inspection process for conducting inspections, the inspection process comprising:
    receiving a work order from a web-based system operated by an inspection facilitator, the work order including a plurality of inspection items in list, the list being retrievable by selecting a related asset from a map, list being selectable by the inspector, wherein the map is at least one of a plan view, sky view and 3-dimensional rendering of a facility and wherein each of the plurality of assets are represented on the map according to a corresponding physical location of each of the plurality of assets in the facility;

the inspection process further, upon a selection of an item by the inspector, bringing up a form including standardized questions relating to the condition of the inspection item the standardized questions being made to be unalterable by the inspector using a handheld device on which the standardized questions are presented;

a prepopulation process wherein already-known characteristics regarding the inspection item are automatically included into the form when the form is presented to the inspector, but the included characteristics are made to be alterable by the inspector in the form if they are found to be incorrect;

the process further requiring the inspector to submit answers to the standardized questions, a camera-interfacing process which is turned on by the inspector by interfacing with the handheld computing device, the camera-interfacing process causing a signal to be transmitted by the handheld computing device, the signal enabling interfacing with, and downloading photos from a camera the downloading of photos automatically terminating when the inspector closes the form;

a coating thickness-reading process enabling the handheld to download thickness readings from a thickness reading device, the thickness-reading device determining thickness by sending and receiving waves to determine coating depth, the thickness-reading process then incorporating the thickness readings into the form; and means to archive saved questions and answers for the inspection item by the unique identifier for use in future inspections.

17. The inspection process of claim 16 comprising:

an asset addition process providing an inspector encountering a new, currently omitted item to be added to future inspections.

* * * * *